United States Patent [19]

Mausner

[11] 4,126,674
[45] Nov. 21, 1978

[54] THICKENED AQUEOUS SHAMPOO COMPOSITIONS CONTAINING ENCAPSULATED CONDITIONING AGENTS

[75] Inventor: Jack J. Mausner, East Hills, N.Y.

[73] Assignee: Helena Rubinstein, Inc., New York, N.Y.

[21] Appl. No.: 835,645

[22] Filed: Sep. 22, 1977

Related U.S. Application Data

[63] Continuation of Ser. No. 685,335, May 11, 1976, abandoned.

[51] Int. Cl.$^2$ .......... A61K 7/08; A61K 7/50; C11D 3/46; C11D 17/08
[52] U.S. Cl. .................. 424/31; 252/89 R; 252/90; 252/92; 252/153; 252/171; 252/173; 252/316; 252/545; 252/550; 252/DIG. 5; 252/DIG. 13; 424/37; 424/70
[58] Field of Search .............. 424/16, 31, 36, 70, 424/37; 252/89, 90, 92, 153, 162, 170, 171, 173, 544, 545, 550, 316, DIG. 5, DIG. 13

[56] References Cited

U.S. PATENT DOCUMENTS

| 3,011,950 | 12/1961 | Mehaffey | 252/539 X |
|---|---|---|---|
| 3,341,466 | 9/1967 | Brynko | 252/316 |
| 3,726,803 | 4/1973 | Bayless | 252/316 |
| 3,798,179 | 3/1974 | Hellyer | 252/535 |
| 3,829,563 | 8/1974 | Barry | 424/70 |
| 3,932,610 | 1/1976 | Rudy | 424/70 |
| 3,950,510 | 4/1976 | Adams | 424/70 |

FOREIGN PATENT DOCUMENTS 1,268,316   5/1968   Fed. Rep. of Germany ............ 424/70

OTHER PUBLICATIONS

"Microscopic Capsules of Oil in Shampoo for Dry Hair", Norda Schimmel Briefs, No. 405, Jan. 1969, 3 pages.
Schmolka, I. R.: "Applications of Pluronic Polyols in the cosmetic Industry", Am. Perfumer & Cosmetics, vol. 82, Jul. 1967, pp. 25–30.

Primary Examiner—Dennis L. Albrecht
Attorney, Agent, or Firm—Burgess, Ryan and Wayne

[57] ABSTRACT

There are disclosed compositions of matter which would provide, in one single application, the dual effects of shampooing and conditioning the hair. The compositions are aqueous compositions containing a mixture of humectants, surfactants, chelating agents, thickening agents and capsules of hair conditioning agents suspended therein.

11 Claims, No Drawings

THICKENED AQUEOUS SHAMPOO COMPOSITIONS CONTAINING ENCAPSULATED CONDITIONING AGENTS

CROSS REFERENCE TO RELATED APPLICATION

This is a continuation of copending application Ser. No. 685,335, filed May 11, 1976, now abandoned.

BACKGROUND OF THE INVENTION

Shampoo compositions utilizing various surfactants are known in the art. Generally, the consumer applies small portions of the shampoo to the hair and works it into a lather with water. Thereafter, the lather is removed by rinsing with water. The detergent action of the surfactants present in these compositions will often times cause the hair to lose its lustre and suppleness thereby rendering the hair unruly and unmanageable. Consequently, to restore the hair to its original luster and suppleness after cleansing with the shampoo, there is required an additional application of a hair conditioning composition. That is to say, a two-step operation, i.e., the cleansing of the hair with the shampoo and of the restoration with a conditioning agent of the hair to its original luster and manageability is needed.

SUMMARY OF THE INVENTION

The present invention relates to a single unique composition providing the desired dual action of shampooing and hair conditioning. This composition comprises together with other materials, a combination of a surfactant or a combination of surfactants and discrete and visible particles of hair conditioning agents in an aqueous vehicle. The surfactants are the active ingredients providing the shampooing effect. Suitable surfactants are anionic surfactants such as, for example, triethanolamine lauryl sulfate alone or in combination with a non-ionic surfactant such as polyoxyethylene polyoxypropylene polyoxyethylene and a cationic surface active agent. The aqueous compositions containing these surfactants are thickened by the incorporation therein of thickening agents such as a carboxy vinyl polymer. The hair and scalp conditioning effect is provided by incorporating into the aqueous thickened compositions, selected amounts of an encapsulated mineral oil or other conditioning ingredients. The composition of this invention occurs in the unique form of a clear suspension containing visible capsules of hair conditioning agent.

DETAILED DESCRIPTION OF THE INVENTION

The compositions of this invention are aqueous in nature. Surfactants, suitably anionic in nature, alone or in combination with non-ionic and cationic surfactants are present usually in an amount of from about 5% by weight to about 25% by weight of the composition. The precise combination of these surfactants may be varied depending upon the nature of the hair to be treated, the amount of lather desired and the degree of conditioning. That is to say, if the compositions are applied to oily hair, the amount of surfactants may be increased. The treatment, on the other hand, for normal or dry hair requires less surfactants. In short, the amount of the surfactant in the composition varies depending upon the nature of the surfactant chosen and the condition of the hair to be treated. For example, in formulating a shampoo for normal hair, a mixture of about six parts by weight of polyoxyethylene polyoxypropylene polyoxyethylene is used. On the other hand, if oily hair is to be treated, the amount of the triethanolamine lauryl sulfate is increased to an amount of about 30% by weight of the composition.

Among the surfactants which may be advantageously employed in the compositions of the present invention, are those disclosed in McCutchen's Handbook of Detergents. One group of surfactants is the non-ionic surfactants which include, for example, condensates of alkylene oxide as well as groups having an organic hydrophobic compound with an active hydrogen. Suitably, polyoxyethylene sorbitan monostearate can be used. The next group of surfactants are the anionic surfactants and illustratively, alkyl benzene sulphonates such as sodium dodecyl sulphonate, primary alkyl sulphates such as, for example, triethanolamine lauryl sulfate and also secondary alkyl sulfates such as, for example, diethanolamine lauryl sulfates. The anionic surfactants can be used in amounts varying between 0.5 and 20%, by weight of the composition. The last group of surfactants are the cationic surfactants and these materials can be used in amounts up to about 3.0%, by weight, of the composition. Suitably, cationic surfactants such as distearyl dimethyl ammonium chloride, dilauryl dimethyl ammonium chloride and N-cetyl pyridinium bromide, can be used.

To improve the applicability as well as the wettability of the shampoo composition, additives such as, for example, humectants, emollients and chelating agents are included. Fragrances, coloring materials, and preservatives as well as U.V. light absorbers are also added to increase the stability and cosmetic elegance of the composition.

Among the humectants, there may be mentioned, for example, polyhydroxy alcohols such as propylene glycol, glycerine, and the like, and these materials can be used in amounts up to about 15%, by weight of the composition.

Illustrative of the U.V. light absorber used, is, for example, 2,2'-dihydroxy-4-methoxy benzophenone. A small amount, typically, about 0.1%–0.5% by weight is used. Typical chelating agents are the disodium salt of ethylenediamine tetra acetic acid (EDTA) and citric acid which are known in the art. These materials can be used in amounts up to about 0.7%, by weight of the composition.

Included in the composition, are emollients varying in amount from 0.5 to about 5%, by weight of the composition.

In a typical practice of the present composition, a slurry of the thickening agent for example, a carboxy vinyl polymer, available under the trade name Carbopol 940, is dispersed in water by slowly mixing, preferably without aeration. The resulting suspension is heated to a uniform temperature of about 85° C. To this is added the solution of surfactants also at a temperature of about 85° C. Again, the mixing is accomplished without aeration. After the mixture has cooled to room temperature, a suitable base typically, triethanolamine, is added until a clear gel is obtained.

The hair conditioning agents, i.e., gelatin capsules containing mineral oil, are then dispersed in the resultant clear gel. The aforementioned optional additional ingredients, e.g. U.V. light absorber, formalin, chelating agents, are dissolved in water and combined with the aforesaid surfactant solution.

The coloring materials and fragrances are added to the final composition.

The compositions of this invention occur in the form of a clear gel with visible capsules of hair conditioning agents suspended therein. In use, the consumer wets the hair and applies about 5 to 20 ml of this composition of this invention into the hair and works up the lather. After about a 5 to 10 minute lathering treatment, the lather is rinsed off with water and the hair is dried. It has been found, following such a treatment that the hair is not only effectively cleansed but also conditioned simultaneously.

If a more viscous gel is desired, additional carboxy vinyl polymer may be added alone or in combination with other thickening agents such as hydroxy ethyl cellulose, hydroxy propyl cellulose and so on. The amount of the additional thickening agent to be added is within the purview of those skilled in the art.

In order to illustrate further the practice of the present invention, the following examples are included.

EXAMPLE 1

Shampoo-Hair Conditioning compositions for Normal Hair 28.5 grams of Carbopol 940 are slurried in about 80 ml. of water and heated to a temperature of about 90° C. with gentle mixing. In a separate kettle, 6 grams of triethanolamine lauryl sulfate, 0.9-grams of polyoxyethylene polyoxypropylene polyoxyethylene, 0.10 grams of 2,2-dihydroxy-4-methoxy benzophenone, 180 ml. of a 25% aqueous solution of hydrochloric acid, 0.30 grams of EDTA and 0.15 grams of a cationic cellulose derivative,* 1 gram of quaternized hydroxy alkyl amino gluconamide are dissolved in sufficient water, accompanied by heat, at a temperature of about 80°–90° C. When a solution is obtained, the solution is combined with the Carbopol slurry at approximately 80°–90° C. The mixture is gently mixed without introducing aeration. When the product has cooled to room temperature, about 0.60 ml. of triethanolamine is added to obtain a clear gel. Thereafter, 0.3 grams of gelatine capsules containing mineral oil are added, accompanied by mixing.

* a hydroxy ethyl cellulose modified with a quaternary ammonium cation on approximately every other anhydro glucose unit. This product is manufactured and sold by the Union Carbide Company.

0.20 ml. of formalin, 1.50 ml. of ethyl alcohol, and 0.3 grams of fragrances are mixed into the aforesaid product.

Since water may be lost, by evaporation, during preparation, the final volume of the product is adjusted to 100% with more water, if needed. The product occurs in the form of a clear gel with visible capsules of hair conditioning agents suspended therein.

The carboxy vinyl polymer is used in an amount up to about 5%, by weight of the composition.

EXAMPLE 2

The following formulation is designed to treat dry hair:

| Material | % by weight of composition |
| --- | --- |
| Propylene glycol | 8.00 |
| Cationic cellulose derivative | 2.50 |
| Triethanolamine lauryl sulfate | 3.00 |
| Disodium salt of a dicarboxylated imidazoline derivative | 14.50 |
| Gelatine capsules containing mineral oil | 0.40 |
| Carboxy vinyl polymer (thickened) | 29.50 |
| Quaternized hydroxy alkyl amino gluconamide | 2.00 |
| Triethanolamine | 0.30 |
| 2,2-dihydroxy-4-methoxy benzophenone | 0.10 |
| Hydrochloric acid (25% aq. soln.) | 0.80 |
| Formalin | 0.20 |
| Disodium salt of ethylenediamine tetra acetic acid (EDTA) | 0.30 |
| Polyoxyethylene polyoxypropylene polyoxyethylene | 0.90 |
| Ethyl alcohol SD-40 | 1.50 |
| Perfume | 0.35 (approx.) |
| Colors  D.C. Green No. 8 | |
| D.C. Green No. 5 | 0.1–3% |
| Water up to | 100% |

The above formulation is prepared in accordance with the procedure as set out in Example 1.

Other suitable water-soluble colors can also be used.

EXAMPLE 3

The following ingredients are utilized in the preparation of a formulation for oily hair;

| Material | % by weight of composition |
| --- | --- |
| Propylene glycol | 8.00 |
| Triethanolamine lauryl sulfate | 30.00 |
| Gelatin capsules containing mineral oil | 0.20 |
| Carboxy vinyl polymer | 40.00 |
| Triethanolamine | 1.10 |
| 2,2'-dihydroxy-4-methoxy benzophenone | 0.10 |
| Formalin | 0.20 |
| Disodium salt of ethylenediamine tetra acetic acid | 0.30 |
| Hydroxyethylcellulose | 0.40 |
| Polyoxyethylene polyoxypropylene polyoxyethylene | 0.90 |
| Ethyl alcohol SD-40 | 1.50 |
| Fragrance | 0.35 (approx.) |
| Colors  D.C. Red No. 33 | |
| D.C. Green No. 5 | 0.1–3% |
| Water  up to | 100% |

Again, the above formulation is prepared by the procedure as set out in Example 1.

Additionally, other water-soluble colors can suitably be used.

The conditioning agents present in the instant compositions are encapsulated oils, the capsules being visible, that is, macroscopic and varying in size up to about 0.3 mm. A suitable encapsulated oil is the encapsulated mineral oil, a well known commercially available product produced by National Cash Register Company, the capsules being prepared by the process disclosed in National Cash Register U.S. Pat. No. 3,341,466 granted Sept. 12, 1967 which is concerned with making strong-walled large size, or macro, capsules, and U.S. Pat. No. 3,726,803 granted Apr. 10, 1973 which is concerned with making the capsule walls hydrophobic, insoluble, and substantially unswellable in liquids which either dissolve or swell the wall material before the treatment. Oils other than mineral oil can be used such as, for example, isopropyl myristate, lipid-like oils, fatty acid esters, hydrocarbon oils, and the like. The encapsulated mineral oil is used in amounts varying up to about 2.0% by weight of the composition.

What is claimed is:

1. A shampoo-hair conditioning composition, comprising, in combination:

(A) an effective amount of at least one surfactant for shampooing the hair, said surfactant comprising triethanolamine lauryl sulfate and polyoxyethylene polyoxypropylene polyoxyethylene in a ratio of from 3:0.9 to 30:0.9, (B) discrete visible capsules of an encapsulated oil in an amount effective to condition the hair, (C) a thickened acqueous vehicle comprising an effective amount of a carboxy vinyl polymer thickener.

2. A composition according to claim 1, containing about 6% by weight of triethanolamine lauryl sulfate and about 0.90% by weight of polyoxyethylene polyoxypropylene polyoxyethylene.

3. A composition according to claim 1, containing about 3% by weight of triethanolamine lauryl sulfate and about 0.90% by weight of polyoxyethylene polyoxypropylene polyoxyethylene.

4. A composition according to claim 1 containing about 30% by weight of triethanolamine lauryl sulfate and about 0.90% parts by weight of polyoxyethylene polyoxypropylene polyoxyethylene.

5. A composition according to claim 1 comprising about 0.2 to 2% by weight of gelatin capsules containing an oil.

6. A composition according to claim 1 wherein said thickened aqueous vehicle comprises a carboxy vinyl polymer neutralized with a base.

7. A composition according to claim 6 containing about 28.5 to 40% by weight of carboxy vinyl polymer.

8. A composition according to claim 1 wherein the oil is a mineral oil.

9. A composition according to claim 1 comprising, in percent by weight:

| | |
|---|---|
| a carboxy vinyl polymer | 28.5 |
| triethanolamine lauryl sulfate | 6.0 |
| polyoxyethylene-polyoxypropylene-polyoxyethylene | 0.9 |
| triethanolamine | 0.60 |
| oil-containing capsules | 0.30 |
| water | to make 100. |

10. A composition according to claim 1, comprising, in percent by weight:

| | |
|---|---|
| a carboxy vinyl polymer | 29.5 |
| triethanolamine lauryl sulfate | 3.0 |
| polyoxypropylene-polyoxyethylene-polyoxypropylene | 0.9 |
| triethanolamine | 0.30 |
| oil-containing capsules | 0.40 |
| water | to make 100 |

11. A composition according to claim 1, comprising, in percent by weight:

| | |
|---|---|
| a carboxy vinyl polymer | 40 |
| triethanolamine lauryl sulfate | 30 |
| polyoxypropylene-polyoxyethylene-polyoxypropylene | 0.90 |
| triethanolamine | 1.10 |
| oil-containing capsules | 0.20 |
| water | to make 100. |

* * * * *